United States Patent
Fuji et al.

(10) Patent No.: US 8,039,645 B2
(45) Date of Patent: Oct. 18, 2011

(54) METHOD FOR CONTINUOUSLY PRODUCING 2,5-DIHYDROFURAN

(75) Inventors: Junichi Fuji, Ibaraki (JP); Shigeru Okano, Chiba (JP); Katsushi Nagareda, Ibaraki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 12/529,548

(22) PCT Filed: Mar. 5, 2008

(86) PCT No.: PCT/JP2008/053917
§ 371 (c)(1),
(2), (4) Date: Sep. 2, 2009

(87) PCT Pub. No.: WO2008/111446
PCT Pub. Date: Sep. 18, 2008

(65) Prior Publication Data
US 2010/0087665 A1   Apr. 8, 2010

(30) Foreign Application Priority Data
Mar. 6, 2007 (JP) ................................. 2007-055140

(51) Int. Cl.
*C07D 307/02* (2006.01)

(52) U.S. Cl. ....................................... 549/209; 549/507

(58) Field of Classification Search .................. 549/507, 549/509
See application file for complete search history.

(56) References Cited

U.S. PATENT DOCUMENTS

| | | | |
|---|---|---|---|
| 3,165,536 A | 1/1965 | Anilin | |
| 4,196,130 A | 4/1980 | Huchler et al. | |

FOREIGN PATENT DOCUMENTS

| | | |
|---|---|---|
| DE | 1 211 219 | 2/1966 |
| JP | 56 73080 | 6/1981 |
| JP | 9 110850 | 4/1997 |
| JP | 11 349581 | 12/1999 |

*Primary Examiner* — Victor Oh

(74) *Attorney, Agent, or Firm* — Oblon, Spivak, McClelland, Maier & Neustadt, L.L.P.

(57) ABSTRACT

The method of the invention for continuously producing 2,5-dihydrofuran includes subjecting cis-2-butene-1,4-diol to liquid-phase dehydration-cyclization reaction in the presence of alumina, characterized in that the sum of the concentration of carbonyl compounds present in the reaction system and the concentration of acetal compounds present in the reaction system is controlled to fall within a range of 0.1 to 2 mol/L, provided that the concentration of the acetal compounds is calculated in terms of acetal groups, the concentrations being determined on the basis of the total amount of the reaction mixture. According to the method, 2,5-dihydrofuran, which is useful as a raw material or intermediate for producing pharmaceuticals, agrochemicals, raw materials of polymers, etc., can be continuously produced. The method can prevent inactivation of γ-alumina and is advantageous for long-term production on an industrial scale.

14 Claims, No Drawings

METHOD FOR CONTINUOUSLY PRODUCING 2,5-DIHYDROFURAN

This application is a 371 of PCT/JP2008/053917, filed Mar. 5, 2008.

TECHNICAL FIELD

The present invention relates to a method for continuously producing 2,5-dihydrofuran, which is useful as a raw material or intermediate for producing pharmaceuticals, agrochemicals, raw materials of polymers, etc.

BACKGROUND ART

There have been known methods for producing cyclic ethers; for example, a method of producing 2,5-dihydrofuran through dehydration-cyclization of cis-2-butene-1,4-diol in the presence of a hydrogensulfate salt or in the presence of sulfuric acid and a base (see Patent Document 1); a method of producing 2,5-dihydrofuran including causing vaporized cis-2-butene-1,4-diol to pass through an alumina-catalyst-containing tube with helium and hydrogen (see Non-Patent Document 1); a method of continuously producing 2,5-dihydrofuran through feeding cis-2-butene-1,4-diol to a reactor in the presence of an aluminum oxide catalyst for subjecting the diol to dehydration-cyclization reaction at ambient pressure and 170 to 220° C. (see Patent Document 2); and a method of producing a cyclic ether including subjecting a saturated $\alpha,\omega$-diol to dehydration-cyclization reaction in the presence of an aluminum oxide which has received a specific treatment (see Patent Document 3).

Non-Patent Document 1:
Industrial Eng. Chem. Product Res.& Dev., 1973, Vol. 12, No. 3, p. 184-189

Patent Document 1: Japanese Patent Application Laid-Open (kokai) No. 1997-110850

Patent Document 2: German Patent No. 1,211,219

Patent Document 3: Japanese Patent Application Laid-Open (kokai) No. 1981-73080

DISCLOSURE OF THE INVENTION

Problems to be Solved by the Invention

The method disclosed in Patent Document 1 has a problem that a reactor made of an expensive material such as Hastelloy (registered trademark) must be employed in order to prevent corrosion, which would otherwise occurs in a generally employed reactor made of iron or stainless steel. In addition, when the present inventors previously carried out the method disclosed in Patent Document 1, by-products derived from cis-2-butene-1,4-diol increased during continuous production for a long period of time, considerably lowering the catalytic activity and making long-term continuous production difficult. In the method disclosed in Non-Patent Document 1, expensive helium gas must be employed, elevating production cost. Thus, this method is not preferred in the production on an industrial scale. Also, Non-Patent Document 1 never describes the effects of carbonyl compounds and acetal compounds which are by-produced during the course of reaction. Through the method disclosed in Patent Document 2, good reaction results, that are selectivity of 95% or more, can be attained. However, Patent Document 2 only discloses reaction results from start of the reaction to 10 hours after the start. Thus, the present inventors actually carried out the same production on the basis of the method disclosed in Patent Document 2. As a result, although good reaction results were obtained during a short reaction period, the catalytic activity decreased in continuous production for 80 hours or longer (see, for example, Comparative Example 1 of the present specification). Patent Document 3 does not disclose that by-products formed during reaction employing unsaturated $\alpha,\omega$-diol as a starting material adversely affects the reaction, when the reaction is continuously performed for a long period of time. Also, Patent Document 3 never discloses the resolution of the problem.

Thus, an object of the present invention, for solving the aforementioned problems, is to provide a method for continuously producing 2,5-dihydrofuran for a long period of time and in an industrially advantageous manner.

Means for Solving the Problems

According to the present invention, the aforementioned object can be attained by the following.

[1] A method for continuously producing 2,5-dihydrofuran, comprising subjecting cis-2-butene-1,4-diol to liquid-phase dehydration-cyclization reaction in the presence of alumina, characterized in that the sum of the concentration of carbonyl compounds present in the reaction system and the concentration of acetal compounds present in the reaction system is controlled to fall within a range of 0.1 to 2 mol/L, provided that the concentration of the acetal compounds is calculated in terms of acetal groups, the concentrations being determined on the basis of the total amount of the reaction mixture.

[2] The method for continuously producing 2,5-dihydrofuran as described in [1] above, wherein the sum of the concentration of carbonyl compounds present in the reaction system and the concentration of acetal compounds present in the reaction system is controlled to fall within a range of 0.5 to 1.5 mol/L, the concentrations being determined on the basis of the total amount of the reaction mixture.

[3] The method for continuously producing 2,5-dihydrofuran as described in [1] or [2] above, wherein the reaction is carried out while cis-2-butene-1,4-diol is continuously or intermittently fed to the reactor, and the formed 2,5-dihydrofuran, water, and a portion of by-products are distilled out.

[4] The method for continuously producing 2,5-dihydrofuran as described in any one of [1] to [3] above, wherein the reaction is continuously carried out for 80 hours or longer.

Effects of the Invention

According to the present invention, 2,5-dihydrofuran, which is useful as a raw material or intermediate for producing pharmaceuticals, agrochemicals, raw materials of polymers, etc., can be produced consistently in an industrially advantageous manner.

BEST MODES FOR CARRYING OUT THE INVENTION

A characteristic feature of the present invention resides in that, when cis-2-butene-1,4-diol is subjected to dehydration-cyclization reaction in the presence of alumina, the sum of the concentration of carbonyl compounds present in the reaction system and the concentration of acetal compounds present in the reaction system is controlled to fall within a range of 0.1 to 2 mol/L (in the present specification, the concentration of the acetal compounds is calculated in terms of acetal groups), the concentrations being determined on the basis of the total amount of the reaction mixture. As used herein, the term "reaction mixture" refers to a liquid mixture containing cis-2-butene-1,4-diol, all by-products formed during the course of the reaction, an optionally added solvent (i.e., the entirety of the liquid mixture contained in the reactor). Unless otherwise specified, the "reaction mixture" contains 2,5-dihydrofuran, which is a target product. The term "continuously" refers to a reaction mode in which the reaction is not completed in one batch but is performed many times without changing the alumina catalyst, or a continuous reaction mode.

Examples of carbonyl compounds present in the reaction system include crotonaldehyde and 4-hydroxybutanal.

Examples of acetal compounds present in the reaction system include a cis-2-butene-1,4-diolacetal compound of crotonaldehyde, 4-hydroxytetrahydrofuran, and compounds formed through further reaction between crotonaldehyde and 4-hydroxybutanal and represented by the following structural formulas:

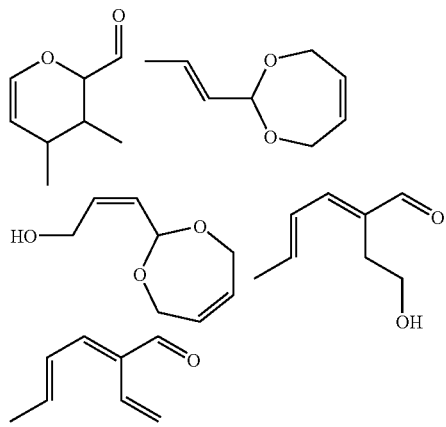

These carbonyl compounds and acetal compounds are by-produced in the course of the reaction.

In the present invention, in addition to the aforementioned carbonyl compounds and acetal compounds, ether compounds are also produced as by-products. Examples of such ether compounds include bis(4-hydroxy-2-butene)ether. However, quite surprisingly, the concentration of ether compounds (hereinafter may be referred to as ether compound concentration) does not affect the reaction in the present invention, and the object of the invention can be attained only through controlling the sum of the concentration of carbonyl compounds and that of acetal compounds in the reaction mixture to fall within a range of 0.1 to 2 mol/L.

As used herein, the aforementioned carbonyl compounds, acetal compounds, ether compounds, and other by-produced compounds may be collectively referred to as "by-products." Among these by-products, those having a low-boiling point (e.g., crotonaldehyde, 4-hydroxybutanal, furan, 2,3-dihydrofuran, tetrahydrofuran, crotonaldehyde, and 4-hydroxybutanal) may be referred to as "low-boiling-point by-products" or "a part of the by-products."

The concentration of cis-2-butene-1,4-diol in the reaction mixture (hereinafter may be referred to as "cis-2-butene-1,4-diol concentration") is preferably 20 to 100 mass % with respect to the entirety of the reaction mixture, more preferably 50 to 99 mass %. When the concentration is 20 mass % or higher, the amount of 2,5-dihydrofuran formed in a unit time is sufficient, which is preferred. No particular limitation is imposed on the method for determining the cis-2-butene-1,4-diol concentration of the reaction mixture, and it may be determined through, for example, gas chromatography (measurement conditions, see the Examples hereinbelow). In the case where the distillation rate of 2,5-dihydrofuran is measured, the variation in cis-2-butene-1,4-diol concentration in the reaction mixture during the reaction is preferably maintained to fall within a range of 30 mass % or less, to thereby facilitate determination of the activity of alumina from the rate of formation of 2,5-dihydrofuran. In contrast, when the variation in cis-2-butene-1,4-diol concentration is significant, the variation affects the rate of formation of 2,5-dihydrofuran, making determination of the activity of alumina difficult, which is not preferred.

Examples of the alumina species include γ-alumina, δ-alumina, χ-alumina, η-alumina, and ρ-alumina. Of these, γ-alumina is preferably used. The alumina species may contain alkali metals such as sodium and potassium; alkaline earth metals such as magnesium and calcium; and other impurities such as silicon, sulfur, copper, iron, chromium, and manganese. From the viewpoint of selectivity to 2,5-dihydrofuran, the impurity amount is preferably 0 to 5 mass % with respect to alumina.

No particular limitation is imposed on the form of the alumina catalyst, and it may be selected from powder, pellets, cylinders, etc.

When the reaction is performed in the below-mentioned liquid-phase suspension state, generally, the amount of alumina used in the invention is preferably 0.1 to 20 mass % with respect to the reaction mixture from the viewpoints of activity of alumina and fluidity of the reaction mixture. When the reaction is performed by means of the below-mentioned liquid-phase fixed bed, the amount of alumina may be appropriately predetermined in accordance the dimensions of the catalyst tank.

The present invention may be performed in the presence or absence of solvent. No particular limitation is imposed on the solvent, so long as the solvent does not adversely affect the reaction. Examples of the solvent include saturated hydrocarbons such as dodecane; and aromatic hydrocarbons such as cumene. When the reaction is performed in the presence of solvent, the amount of the solvent is preferably 1 to 50 mass % with respect to the reaction mixture.

No particular limitation is imposed on the reaction temperature, and the temperature is generally 100 to 300° C. From the viewpoints of productivity and suppression of side reaction caused by isomerization of starting cis-2-butene-1,4-diol, the reaction temperature is preferably 160 to 240° C., more preferably 170 to 230° C. No particular limitation is imposed on the reaction pressure, so long as cis-2-butene-1,4-diol maintains the liquid form at the reaction temperature. The reaction pressure is generally 80 to 120 kPa, preferably ambient pressure. The present invention may be carried out in an inert gas atmosphere such as nitrogen or argon.

The reaction of the present invention may be carried out in liquid-phase suspension or by means of a liquid-phase fixed bed. As used herein, the former may be referred to as "liquid-phase suspension reaction," and the latter "liquid-phase fixed bed reaction."

In one embodiment of liquid-phase suspension reaction, alumina powder, cis-2-butene-1,4-diol, and optional solvent are fed to a reactor, and the mixture is allowed to react at predetermined temperature and pressure in an inert gas atmosphere such as nitrogen or argon.

In one embodiment of liquid-phase fixed bed reaction, a reaction mixture is caused to be in contact with a pellet-form or cylinder-shape alumina catalyst securely placed in a tank-type reactor, or a reaction mixture is caused to pass through a multi-tube reactor which supports the alumina catalyst.

Of these, liquid-phase fixed bed reaction is preferred, since the fixed bed reaction mode does not cause wearing of the reactor, which would otherwise be caused by abrasion of the reactor with stirred alumina.

In the present invention, the reaction is performed "continuously". In one embodiment (A), firstly, the reaction is performed in a batch manner. When percent conversion is in excess of 10%, more preferably in excess of 50%, the reaction mixture is removed from the reactor. Then, 2,5-dihydrofuran, water, and by-products are removed from the reaction mixture, and cis-2-butene-1,4-diol and alumina are recovered. The recovered components are recycled in the reaction of the present invention (another cis-2-butene-1,4-diol may be added to the reaction system), whereby the reaction is continued. In an alternative embodiment (B), cis-2-butene-1,4-diol is continuously or intermittently fed to a reactor where alumina and the relevant reaction mixture are present, and the formed 2,5-dihydrofuran, water, and by-products are preferably removed in a continuous manner.

In the aforementioned continuous manner, as mentioned hereinbelow, the reaction mixture is preferably removed from the reactor so that the sum of the concentration of carbonyl compounds present in the reaction mixture and the concentration of acetal compounds present in the reaction mixture is controlled to fall within a range of 0.1 to 2 mol/L.

In the present invention, as mentioned above, carbonyl compounds and acetal compounds are present as, for example, by-products, in the reaction system during the course of the reaction. The sum of the concentration of carbonyl compounds present in the reaction mixture and the concentration of acetal compounds present in the reaction mixture is controlled to fall within a range of 0.1 to 2 mol/L, preferably 0.3 to 2 mol/L, more preferably 0.3 to 1.7 mol/L, still more preferably 0.5 to 1.7, particularly preferably 0.5 to 1.5 mol/L. When the sum of the concentration of carbonyl compounds present in the reaction mixture and the concentration of acetal compounds present in the reaction mixture is less than 0.1 mol/L, the reaction time must be considerably shortened. If the reaction is performed for a long period of time, the step of removing carbonyl compounds and acetal compounds from the reaction system increases the operation load. Thus, such a small sum of the concentrations is not advantageous from the viewpoint of operation on an industrial scale. When the sum of the concentrations is in excess of 2 mol/L, contact between alumina and carbonyl compounds and/or acetal compounds reduces the activity of alumina, thereby failing to operate the reactor for a long period of time.

No particular limitation is imposed on the method of quantitating carbonyl compounds and acetal compounds, and an analyzer such as a gas chromatograph or a liquid chromatograph may be employed. Alternatively, the hydroxylamine hydrochloride method (see the Examples of the specification and Shin-Jikken Kagaku Koza, Vol. 13, 3rd edition, Organic Structure [I], p. 57-58) may be employed. Among these methods, the hydroxylamine hydrochloride method is preferred, since a variety of carbonyl compounds and acetal compounds can be collectively quantitated.

Examples of the specific approach for maintaining the sum of the concentration of carbonyl compounds present in the reaction mixture and the concentration of acetal compounds present in the reaction mixture at 0.1 to 2 mol/L include the following:

(1) the distillation separation method in which the reaction mixture contained in the tank-type reactor is distilled to thereby remove carbonyl compounds and acetal compounds from the reactor;

(2) the liquid renewal method in which a portion of the reaction mixture is taken from the reactor, and if present, alumina is appropriately removed from the taken reaction mixture, followed by returning the separated alumina to the reactor, and a material such as cis-2-butene-1,4-diol is added to the reactor, whereby the sum of the concentration of carbonyl compounds and that of acetal compounds is reduced;

a preferred mode of method (2) in which the reaction mixture from which alumina has been removed is distilled, to thereby remove carbonyl compounds and acetal compounds and separate cis-2-butene-1,4-diol, and the thus-separated cis-2-butene-1,4-diol is returned to the reactor;

(3) the carbonyl adsorption method in which the reaction mixture is circulated through the reactor along with an adsorbent which can adsorb carbonyl species (e.g., anion-exchange resin); and (4) the membrane separation method in which the reaction mixture is circulated through the reactor and through a separation membrane made of polyvinylpyridine or halide-crosslinked polyvinylpyridine.

Particularly, a combination of the distillation separation method (1) and the liquid renewal method (2) is preferred, from the viewpoint of high efficiency. In a specific embodiment, alumina is securely placed in the tank-type reactor, and the reaction is performed while 2,5-dihydrofuran, water, low-boiling-point carbonyl compounds (crotonaldehyde, 4-hydroxybutanal, etc.), and acetal compounds are removed through distillation (distillation temperature: 90 to 100° C./ambient pressure). Simultaneously, a portion of the reaction mixture is removed, and a material such as cis-2-butene-1,4-diol is added to the reactor, whereby the sum of the concentration of carbonyl compounds present in the reaction mixture and the concentration of acetal compounds present in the reaction mixture can be maintained at 0.1 to 2 mol/L. Through distillation of the thus-removed reaction mixture, carbonyl compounds, acetal compounds, and cis-2-butene-1,4-diol can be separated. The thus-separated cis-2-butene-1,4-diol may be returned to the reactor.

The thus-obtained reaction mixture is distilled, to thereby separate and purify 2,5-dihydrofuran. Furthermore, the residual liquid from which 2,5-dihydrofuran has been removed through distillation and which contains cis-2-butene-1,4-diol may be reused as a starting material of the present invention.

Notably, cis-2-butene-1,4-diol, which is a starting material employed in the present invention, may be produced through Reppe reaction between acetylene and formaldehyde to give 2-butyne-1,4-diol and selective hydrogenation of 2-butyne-1,4-diol in the presence of a palladium catalyst. The hydrogenation may be carried out according to the method described in, for example, Japanese kohyo Patent Publication No. 1998-502363. Specifically, a 50-mass % aqueous butynediol solution, which has been produced through Reppe reaction, and a palladium catalyst (150 mg) are placed in an autoclave, and butynediol is hydrogenated at 100° C. and a hydrogen pressure of 1.8 MPa, to thereby produce cis-2-butene-1,4-diol.

Butanediol (1.6%), acetal compounds (0.3%), and butynediol (0.8%) are formed as by-products. Among them, acetal compounds may be removed through purification/separation. Meanwhile, a carbonyl compound of cis-2-butene-1,4-diol, which can be obtained in an industrial process, has been detected at a level below the detection limit (0.02 mol/L) of the below-mentioned hydroxylamine hydrochloride method.

EXAMPLES

The present invention will next be described in more detail by way of examples, which should not be construed as limiting the invention thereto. In the following Examples, the cis-2-butene-1,4-diol concentration of a reaction mixture and the 2,5-dihydrofuran concentration of a distillate were determined through gas chromatography. The sum of the concentration of carbonyl compounds present in the reaction mixture and the concentration of acetal compounds present in the reaction mixture was determined through the hydroxylamine hydrochloride method.

In the following Examples, gas chromatographic analysis and quantitation based on the hydroxylamine hydrochloride method were performed through the procedures described below. Separately, γ-alumina was charged into a pouch made of Teflon (registered trademark) in the following manner, and the product was used in the Examples and other experiments.
[Gas Chromatographic Analysis Conditions]
Chromatograph: GC-9A (product of Shimadzu Corporation)
Column employed: CBP-1 (length: 50 m, product of Shimadzu Corporation)
Analysis conditions: inlet temperature of 50° C. and detector temperature of 250° C.
Detector: Flame ionization detector (FID)
Temperature elevation: maintaining 50° C. for 10 min, heating at 15° C./min to 250° C., and maintaining 250° C. for 10 min
[Hydroxylamine Hydrochloride Method]

A sample (about 4 g) was added to a 0.5-mol/L hydroxylamine hydrochloride solution [water:ethanol=1:4 (vol. ratio)] (50 mL), followed by stirring for 30 minutes. The formed acid was titrated with 0.5-mol/L aqueous sodium hydroxide, with pH being measured by means of a pH meter having a calomel electrode and a glass electrode. The sum of the concentration of carbonyl compounds and that of acetal compounds was calculated by the following equation.

Sum of the concentration of carbonyl compounds and that of acetal compounds (mol/L)=titration amount (mL)×0.5 (mol/L)/(sample amount (g)/specific gravity (g/mL))

[Filling a Pouch Made of Telfon (Registered Trademark) with γ-alumina]

In the Examples and Comparative Examples, pouches made of Telfon (registered trademark) filled with γ-alumina were employed. The pouches were prepared through the following procedure. Specifically, sheets (6 cm×4 cm) were cut out from a PFA Mesh (tradename, Teflon (registered trademark) mesh) (30 mesh, fiber diameter: 260 μm, opening: 590 μm). Each sheet was folded in two to have a rectangular shape (3 cm×4 cm), and γ-alumina was placed thereon and wrapped in the sheet. Three sides of the sheet were closed by heat-melting, to thereby form a γ-alumina-containing pouch.

Example 1

Liquid-Phase Fixed Bed Reaction

A Teflon (registered trademark) pouch containing E30N4 (γ-alumina, ring-form pellets (inner diameter: 2 mm, outer diameter: 5 mm, height: 3.8 mm), product of Nikki Chemical Co., Ltd.) (14 g) was securely placed in a three-neck flask (capacity: 1,000 mL) equipped with an electromagnetic stirrer and a distillation outlet. The flask was provided with a distillation column (inner diameter: 25 mm×length: 400 mm, no filler, number of theoretical plate (NTP): 2), and a water-cooling reflux condenser was provided at the top of the distillation column.

cis-2-Butene-1,4-diol (500 mL (540 g, 6.1 mol)) was fed to the flask and heated to 195° C. at ambient pressure under nitrogen with stirring. While 2,5-dihydrofuran, water, and low-boiling-point by-products (e.g., crotonaldehyde and 4-hydroxybutanal) were distilled out (93 to 97° C./ambient pressure), cis-2-butene-1,4-diol was continuously fed to the flask so that the volume of the reaction mixture in the flask was maintained at 500 mL. Immediately after start of reaction, the reaction mixture was found to have a cis-2-butene-1,4-diol concentration of 99 mass %.

Sixty hours after start of the reaction, the cis-2-butene-1,4-diol concentration of the reaction mixture present in the reactor reached 50 mass %. At this time, the sum of the concentration of carbonyl compounds and that of acetal compounds was determined through the hydroxylamine hydrochloride method, and was found to be 1.4 mol/L. Eighty hours after start of the reaction, in order to maintain the sum of the concentration of carbonyl compounds and that of acetal compounds at 0.1 to 2 mol/L, an aliquot (100 mL) of the reaction mixture was removed from the flask and wasted (the wasted reaction mixture containing no 2,5-dihydrofuran), and a new aliquot (100 mL) of cis-2-butene-1,4-diol was added to the reactor. At this time, the cis-2-butene-1,4-diol concentration of the reaction mixture present in the reactor reached 60 mass %. Thereafter, the cis-2-butene-1,4-diol concentration of the reaction mixture and the sum of the concentration of carbonyl compounds and that of acetal compounds were determined at appropriate points in time. In the case where the sum of the concentration of carbonyl compounds and that of acetal compounds was found to increase, a portion of the reaction mixture was appropriately removed from the flask and wasted (the wasted reaction mixture containing no 2,5-dihydrofuran), and a new aliquot of cis-2-butene-1,4-diol was added to the reactor, whereby the sum of the concentration of carbonyl compounds and that of acetal compounds was maintained at 0.1 to 2 mol/L. After hour 60 of the reaction, the cis-2-butene-1,4-diol concentration of the reaction mixture was maintained at 49 to 60 mass %. The results are shown in Table 1.

TABLE 1

| Reaction time* (hours) | Distillation rate of DHF (mL/h) | BED concentration of still liquid (mass %) | Sum of the concentration of carbonyl compounds and that of acetal compounds (mol/L) |
| --- | --- | --- | --- |
| 60 | 22 | 50 | 1.4 |
| 80 | 21 | 60 | 1.4 |
| 100 | 23 | 53 | 1.1 |
| 120 | 24 | 60 | 0.8 |
| 140 | 21 | 49 | 1.3 |
| 350 | 20 | 50 | 1.0 |

DHF: 2,5-dihydrofuran
BED: cis-2-buten-1,4-diol
*Start of reaction: at the point in time when distillation of 2,5-dihydrofuran started Comparative Example 1

Liquid-Phase Fixed Bed Reaction

A Teflon (registered trademark) pouch containing E30N4 (γ-alumina, ring-form pellets (inner diameter: 2 mm, outer diameter: 5 mm, height: 3.8 mm), product of Nikki Chemical Co., Ltd.) (14 g) was securely placed in a three-neck flask (capacity: 1,000 mL) equipped with an electromagnetic stirrer and a distillation outlet. The flask was provided with a distillation column (inner diameter: 25 mm×length: 400 mm, no filler, NTP: 2), and a water-cooling reflux condenser was provided at the top of the distillation column.

cis-2-Butene-1,4-diol (500 mL (540 g, 6.1 mol)) was fed to the flask and heated to 195° C. at ambient pressure under nitrogen with stirring. While 2,5-dihydrofuran, water, and low-boiling-point by-products (e.g., crotonaldehyde and 4-hydroxybutanal) were distilled out (93 to 97° C./ambient pressure), cis-2-butene-1,4-diol was continuously fed to the flask so that the volume of the reaction mixture in the flask was maintained at 500 mL. Immediately after start of reaction, the reaction mixture was found to have a cis-2-butene-1,4-diol concentration of 99 mass %.

From start of the reaction to 100 hours after the start of reaction, no control was performed on the carbonyl compound concentration and the acetal compound concentration of the reaction mixture. At the point in time 100 hours after start of the reaction, the sum of the concentration of carbonyl compounds in the reaction mixture and that of acetal compounds in the reaction mixture was found to be 2.3 mol/L, and the cis-2-butene-1,4-diol concentration of the reaction mixture was found to be 30 mass %. Thus, an aliquot (200 mL) of the reaction mixture was removed from the flask and wasted (the wasted reaction mixture containing no 2,5-dihydrofuran), and a new aliquot (200 mL) of cis-2-butene-1,4-diol was added to the reactor, whereby the cis-2-butene-1,4-diol concentration was maintained at 55 mass %. Thereafter, the cis-2-butene-1,4-diol concentration of the reaction mixture and the sum of the concentration of carbonyl compounds and that of acetal compounds were determined at appropriate points in time. In the case where the sum of the concentration of carbonyl compounds and that of acetal compounds was found to increase, a portion of the reaction mixture was appropriately removed from the flask and wasted (the wasted reaction mixture containing no 2,5-dihydrofuran), and a new aliquot of cis-2-butene-1,4-diol was added to the reactor, whereby the sum of the concentration of carbonyl compounds and that of acetal compounds did not exceed 2 mol/L. From the point in time 100 hours after start of the reaction, the cis-2-butene-1,4-diol concentration of the reaction mixture was maintained at 30 to 55 mass %. The results are shown in Table 2.

TABLE 2

| Reaction time* (hours) | Distillation rate of DHF (mL/h) | BED concentration of still liquid (mass %) | Sum of the concentration of carbonyl compounds and that of acetal compounds (mol/L) |
|---|---|---|---|
| 60 | 21 | 48 | 1.5 |
| 80 | 13 | 42 | 2.1 |
| 100 | 9 | 30 | 2.3 |
| 120 | 14 | 52 | 1.1 |
| 140 | 14 | 49 | 1.3 |
| 350 | 13 | 51 | 1.1 |

DHF: 2,5-dihydrofuran
BED: cis-2-buten-1,4-diol
*Start of reaction: at the point in time when distillation of 2,5-dihydrofuran started Comparative Example 2

Liquid-Phase Fixed Bed Reaction

A Teflon (registered trademark) pouch containing E30N4 (γ-alumina, ring-form pellets (inner diameter: 2 mm, outer diameter: 5 mm, height: 3.8 mm), product of Nikki Chemical Co., Ltd.) (14 g) was securely placed in a three-neck flask (capacity: 1,000 mL) equipped with an electromagnetic stirrer and a distillation outlet. The flask was provided with a distillation column (inner diameter: 25 mm×length: 400 mm, no filler, NTP: 2), and a water-cooling reflux condenser was provided at the top of the distillation column.

cis-2-Butene-1,4-diol (500 mL (540 g, 6.1 mol)) was fed to the flask and heated to 195° C. at ambient pressure under nitrogen with stirring. While 2,5-dihydrofuran, water, and low-boiling-point by-products (e.g., crotonaldehyde and 4-hydroxybutanal) were distilled out (93 to 97° C./ambient pressure), cis-2-butene-1,4-diol was continuously fed to the flask so that the volume of the reaction mixture in the flask was maintained at 500 mL.

Sixty hours after start of the reaction, the aforementioned distillation column was changed to a distillation column having higher separating performance (inner diameter: 25 mm, length: 600 mm, filler: Helipack No. 2, NTP: 20). The new distillation column was equipped, at the top thereof, with a water-cooling reflux condenser, so that distillation of low-boiling-point by-products (e.g., crotonaldehyde and 4-hydroxybutanal) was prevented. Under these conditions, distillation was further performed at 195 to 198° C. (distillation temperature at column: 65 to 75° C./ambient pressure). At appropriate points in time, a portion of the reaction mixture was removed from the flask and wasted (the wasted reaction mixture containing no 2,5-dihydrofuran), so that the volume of the reaction mixture in the flask did not exceed 500 mL. No particular control was performed on the concentration of carbonyl compounds and that of acetal compounds in the reaction mixture. As a result, the sum of the concentrations exceeded 2 mol/L. The results are shown in Table 3.

TABLE 3

| Reaction time* (hours) | Distillation rate of DHF (mL/h) | BED concentration of still liquid (mass %) | Sum of the concentration of carbonyl compounds and that of acetal compounds (mol/L) |
|---|---|---|---|
| 60 | 21 | 51 | 1.5 |
| 80 | 18 | 48 | 2.2 |
| 100 | 17 | 53 | 2.3 |
| 120 | 14 | 53 | 2.3 |
| 140 | 10 | 49 | 2.4 |
| 350 | 8 | 50 | 2.5 |

DHF: 2,5-dihydrofuran
BED: cis-2-buten-1,4-diol
*Start of reaction: at the point in time when distillation of 2,5-dihydrofuran started As is clear from Table 1, the amount of distilled 2,5-dihydrofuran during reaction; i.e., the amount of formed 2,5-dihydrofuran, remained virtually unvaried, indicating that constant distillation of the product was ensured. In contrast, as shown in Table 2, when the sum of the concentration of carbonyl compounds in the reaction mixture and that of acetal compounds in the reaction mixture reached 2.1 mol/L (hour 80), the amount of distillated 2,5-dihydrofuran was considerably reduced. Therefore, in Comparative Example 1, the sum of the carbonyl compound concentration and the acetal compound concentration was maintained over 2.0 mol/L from 80 hours after the start to 100 hours after the start, and the activity of γ-alumina was lowered during this period.

As shown in Tables 1 and 3, in contrast to Example 1, the amount of 2,5-dihydrofuran distillated (formed) gradually decreased in Comparative Example 2, and, at hour 140, the amount was about half the amount given in Example 1. Therefore, when reaction was performed for a long period of time under such conditions that the sum of the concentration of carbonyl compounds in the reaction mixture and that of acetal compounds in the reaction mixture exceeded 2.1 mol/L, the activity of γ-alumina was continuously reduced.

Thus, in the production method of the present invention, even when the reaction is continuously performed for a long period of time (e.g., 80 hours or longer, 100 hours or longer, or 120 hours or longer), stability in catalytic activity can be maintained. Such an advantageous effect would become remarkable in the case where 2,5-dihydrofuran is produced in an amount of, for example, ≧60 parts by mass, preferably ≧80 parts by mass, more preferably ≧100 parts by mass, with respect to 1 part by mass of alumina.

As described above, in addition to carbonyl compounds and acetal compounds, by-products present in the reaction mixture include ether compounds. Thus, whether or not the effects of the present invention shown in Example 1 and Comparative Examples 1 and 2 can be attained through control of only the carbonyl compound concentration and the acetal compound concentration in the reaction mixture was confirmed through the following experiments.

Referential Example 1

Effects of By-Products on the Reaction

For the investigation of the activity of alumina, γ-alumina was preliminarily treated with a mixture of dibutylene glycol and cis-2-butene-1,4-diol in the following manner.
Preliminary Treatment:
A Teflon (registered trademark) pouch containing E30N4 (γ-alumina, ring-form pellets (inner diameter: 2 mm, outer diameter: 5 mm, height: 3.8 mm), product of Nikki Chemical Co., Ltd.) (2.5 g) was securely placed in a pressure reactor (capacity: 100 mL). Under nitrogen, cis-2-butene-1,4-diol (35 mL (37.8 g, 0.43 mol)) and dibutylene glycol, an ether compound, (35 mL, (35.4 g, 0.21 mol) equivalent to 2.9 mol/L) were added to the aforementioned reactor, and γ-alumina was completely immersed in the liquid, followed by heating at 180° C. for 10 hours. Subsequently, the mixture was cooled to room temperature, and the Telfon (registered trademark) pouch including γ-alumina was removed from the reactor. The thus-separated pouch was securely placed in a three-neck flask (capacity: 500 mL) equipped with an electromagnetic stirrer. To a first neck of the flask, a distillation column (inner diameter: 25 mm×length: 400 mm, no filler, NTP: 2) was connected, and a water-cooling reflux condenser was connected to the top of the distillation column. A thermometer was set in a second neck, and the third neck was employed as an inlet.
Dehydration-Cyclization Reaction:
cis-2-Butene-1,4-diol (200 mL) was added to the aforementioned flask, and, under nitrogen, heated to 210° C. at ambient pressure. 2,5-Dihydrofuran, water, and low-boiling-point by-products (e.g., crotonaldehyde and 4-hydroxybutanal) were distilled out through the top of the distillation column (97 to 101° C./ambient pressure), whereby the rate of distillation of 2,5-dihydrofuran was analyzed. The results are shown in table 4.

Referential Example 2

The preliminary treatment of Referential Example 1 was repeated, except that dibutylene glycol (70 mL (70.8 g, 0.43 mol), equivalent to 6.1 mol/L) was used instead of cis-2-butene-1,4-diol (35 mL (37.8 g, 0.43 mol)) and dibutylene glycol (35 mL (35.4 g, 0.21 mol)). Other experiments and analyses were performed in a manner similar to that of Referential Example 1. The results are shown in Table 4.

Referential Example 3

The preliminary treatment of Referential Example 1 was repeated, except that cis-2-butene-1,4-diol (63.0 mL (68.0 g, 0.77 mol)) and crotonaldehyde (7.0 mL (6.0 g, 0.09 mol), equivalent to 1.2 mol/L) were used instead of cis-2-butene-1,4-diol (35 mL) and dibutylene glycol (35 mL). Other experiments and analyses were performed in a manner similar to that of Referential Example 1. The results are shown in Table 4.

Comparative Example 3

The preliminary treatment of Referential Example 1 was repeated, except that cis-2-butene-1,4-diol (56.0 mL (60.5 g, 0.69 mol)) and crotonaldehyde (14 mL (12 g, 0.17 mol), equivalent to 2.4 mol/L) were used instead of cis-2-butene-1,4-diol (35 mL) and dibutylene glycol (35 mL). Other experiments and analyses were performed in a manner similar to that of Referential Example 1. The results are shown in Table 4.

Comparative Example 4

The preliminary treatment of Referential Example 1 was repeated, except that crotonaldehyde (70 mL (59 g, 0.85 mol), equivalent to 12 mol/L) was used instead of cis-2-butene-1,4-diol (35 mL) and dibutylene glycol (35 mL). Other experiments and analyses were performed in a manner similar to that of Referential Example 1. The results are shown in Table 4.

Comparative Example 5

The preliminary treatment of Referential Example 1 was repeated, except that acrolein diethyl acetal (70 mL (60 g, 0.46 mol), equivalent to 6.6 mol/L) was used instead of cis-2-butene-1,4-diol (35 mL) and dibutylene glycol (35 mL). Other experiments and analyses were performed in a manner similar to that of Referential Example 1. The results are shown in Table 4.

Comparative Example 6

The preliminary treatment of Referential Example 1 was repeated, except that crotonaldehyde (14 mL (12 g, 0.17 mol), equivalent to 2.4 mol/L) and acrolein diethyl acetal (56 mL (48 g, 0.35 mol), equivalent to 7.4 mol/L) were used instead of cis-2-butene-1,4-diol (35 mL) and dibutylene glycol (35 mL). Other experiments and analyses were performed in a manner similar to that of Referential Example 1. The results are shown in Table 4.

TABLE 4

| Reaction time* (hours) | Distillation rate of DHF (mL/h) | | | | | | |
|---|---|---|---|---|---|---|---|
| | Ref. Ex. 1 | Ref. Ex. 2 | Ref. Ex. 3 | Comp. Ex. 3 | Comp. Ex. 4 | Comp. Ex. 5 | Comp. Ex. 6 |
| 0 | 0 | 0 | 0 | 0 | 0 | 0 | 0 |
| 1.0 | 14.5 | 14.8 | 15.0 | 10.0 | 6.0 | 8.4 | 8.0 |
| 3.5 | 15.0 | 15.0 | 15.0 | 9.6 | 5.9 | 8.4 | 7.9 |
| 6.0 | 14.5 | 14.8 | 15.0 | 9.8 | 5.9 | 8.3 | 7.9 |

DHF: 2,5-dihydrofuran
*Start of reaction: at the point in time when distillation of 2,5-dihydrofuran started As is clear from Table 4, in Comparative Examples 3 to 6, in which a γ-alumina catalyst preliminarily treated in a reaction mixture having a crotonaldehyde and/or acrolein diethyl acetal concentration higher than 2 mol/L was employed, the rate of DHF distillation decreased, indicating a drop in activity of γ-alumina. In contrast, in Referential Examples 1 to 3, in which the sum of the concentration of carbonyl compounds in the reaction mixture and that of acetal compounds in the reaction mixture was 0.1 to 2 mol/L, no heat-induced drop in activity of γ-alumina was observed, regardless of the amount of ether compounds present in the reaction mixture.

Therefore, no effect of the concentration of ether compounds by-produced in the reaction mixture during the course of reaction was observed. Instead, a drop in activity of alumina was confirmed to be attributable only to that the sum of the concentration of carbonyl compounds in the reaction mixture and that of acetal compounds in the reaction mixture exceeded 2 mol/L.

INDUSTRIAL APPLICABILITY

According to the present invention, 2,5-dihydrofuran can be produced consistently in an industrially advantageous manner. The thus-produced 2,5-dihydrofuran can be used as a raw material or intermediate for producing pharmaceuticals, agrochemicals, raw materials of polymers, etc.

What is claimed is:

1. A method for continuously producing 2,5-dihydrofuran, comprising subjecting cis-2-butene-1,4-diol to a liquid-phase dehydration-cyclization reaction in the presence of alumina, wherein the sum of the concentration of carbonyl compounds present in the reaction system and the concentration of acetal compounds present in the reaction system is controlled to fall within a range of 0.1 to 2 mol/L, provided that the concentration of the acetal compounds is calculated in terms of acetal groups, the concentrations being determined on the basis of the total amount of the reaction mixture, and
wherein the reaction is continuously carried out for 80 hours or longer.

2. The method for continuously producing 2,5-dihydrofuran according to claim 1, wherein the sum of the concentration of carbonyl compounds present in the reaction system and the concentration of acetal compounds present in the reaction system is controlled to fall within a range of 0.5 to 1.5 mol/L, the concentrations being determined on the basis of the total amount of the reaction mixture.

3. The method for continuously producing 2,5-dihydrofuran according to claim 1, wherein the reaction is carried out while cis-2-butene-1,4-diol is continuously or intermittently fed to the reactor, and the formed 2,5-dihydrofuran, water, and a portion of by-products are distilled out.

4. The method for continuously producing 2,5-dihydrofuran according to claim 1, wherein the reaction is continuously carried out for 100 hours or longer.

5. The method for continuously producing 2,5-dihydrofuran according to claim 1, wherein the concentration of cis-2-butene-1,4-diol in the reaction mixture is 20 to 100 mass % with respect to the entirety of the reaction mixture.

6. The method for continuously producing 2,5-dihydrofuran according to claim 5, wherein the concentration of cis-2-butene-1,4-diol in the reaction mixture is 50 to 99 mass % with respect to the entirety of the reaction mixture.

7. The method for continuously producing 2,5-dihydrofuran according to claim 1, wherein the amount of alumina is 0.1 to 20 mass % with respect to the reaction mixture.

8. The method for continuously producing 2,5-dihydrofuran according to claim 2, wherein the reaction is carried out while cis-2-butene-1,4-diol is continuously or intermittently fed to the reactor, and the formed 2,5-dihydrofuran, water, and a portion of by-products are distilled out.

9. The method for continuously producing 2,5-dihydrofuran according to claim 2, wherein the reaction is continuously carried out for 100 hours or longer.

10. The method for continuously producing 2,5-dihydrofuran according to claim 3, wherein the reaction is continuously carried out for 100 hours or longer.

11. The method for continuously producing 2,5-dihydrofuran according to claim 5, wherein the reaction is continuously carried out for 100 hours or longer.

12. The method for continuously producing 2,5-dihydrofuran according to claim 6, wherein the reaction is continuously carried out for 100 hours or longer.

13. The method for continuously producing 2,5-dihydrofuran according to claim 7, wherein the reaction is continuously carried out for 100 hours or longer.

14. The method for continuously producing 2,5-dihydrofuran according to claim 8, wherein the reaction is continuously carried out for 100 hours or longer.

* * * * *